(12) United States Patent
Ferguson

(10) Patent No.: US 10,031,104 B2
(45) Date of Patent: Jul. 24, 2018

(54) MOBILE MICRO-LAB FOR CHEMICAL ANALYSIS OF FLUIDS

(71) Applicant: Yes Way Intellectual Holdings, LLC, Portland, OR (US)

(72) Inventor: Kevin M. Ferguson, Beaverton, OR (US)

(73) Assignee: YES WAY INTELLECTUAL HOLDINGS, LLC, Portland, OR (US)

( * ) Notice: Subject to any disclaimer, the term of this patent is extended or adjusted under 35 U.S.C. 154(b) by 320 days.

(21) Appl. No.: 14/737,798

(22) Filed: Jun. 12, 2015

(65) Prior Publication Data
US 2015/0362460 A1 Dec. 17, 2015

Related U.S. Application Data

(60) Provisional application No. 62/011,971, filed on Jun. 13, 2014.

(51) Int. Cl.
*G01N 27/447* (2006.01)
*G01N 27/72* (2006.01)

(52) U.S. Cl.
CPC . *G01N 27/44795* (2013.01); *G01N 27/44721* (2013.01); *G01N 27/44769* (2013.01); *G01N 27/44791* (2013.01)

(58) Field of Classification Search
CPC .......... G01N 27/447; G01N 27/44717; G01N 27/44721; G01N 27/4473; G01N 27/44769; G01N 27/44773; G01N 27/44778; G01N 27/72
See application file for complete search history.

(56) References Cited

U.S. PATENT DOCUMENTS

| | | | | |
|---|---|---|---|---|
| 5,627,643 A | * | 5/1997 | Birnbaum | G01N 27/44721 204/452 |
| 6,432,630 B1 | * | 8/2002 | Blankenstein | B01D 57/02 422/186 |
| 6,825,047 B1 | * | 11/2004 | Woudenberg | B01L 3/50273 422/50 |
| 2006/0066265 A1 | | 3/2006 | Plotz et al. | |

(Continued)

OTHER PUBLICATIONS

L.Svilainis and V. Dumbrava, "Light Emitting Diode Color Estimation: the Initial Study." Measurements 41.1 (2008), 7 pages.

(Continued)

*Primary Examiner* — Susan D Leong
(74) *Attorney, Agent, or Firm* — Marger Johnson

(57) ABSTRACT

A micro-lab includes one or more electrophoresis devices each optically coupled to respective spectrometers and electronic signal processing, analysis and control, with fluids transported via a system of valves, tubes and pumps. The spectrograms are captured by a respective digital cameras, and chemical characteristics including molecular mobility, particle (molecular) charge, molecular weight, particle (molecular) pH, particle (molecular) dielectric, particle (molecular) conductivity, Raman spectrum of each chemical species, IR spectrum of particle (molecular) is determined, and principal component analysis is performed to identify and quantify chemical constituents.

26 Claims, 3 Drawing Sheets

(56) References Cited

U.S. PATENT DOCUMENTS

| | | | |
|---|---|---|---|
| 2006/0254931 A1* | 11/2006 | Lin | G01N 27/02 |
| | | | 205/775 |
| 2008/0166414 A1* | 7/2008 | Hanes | A61K 9/0073 |
| | | | 424/490 |
| 2009/0025489 A1* | 1/2009 | Christensen | G01N 21/645 |
| | | | 73/864 |
| 2010/0294663 A1* | 11/2010 | Weber | G01N 27/44747 |
| | | | 204/451 |
| 2011/0005930 A1* | 1/2011 | Weber | G01N 27/44747 |
| | | | 204/450 |
| 2014/0002481 A1 | 1/2014 | Broughton et al. | |
| 2014/0329699 A1* | 11/2014 | Esfandyarpour | G01N 27/3278 |
| | | | 506/6 |

OTHER PUBLICATIONS

Kong Man Seng, "Trace gas measurement using a web cam spectrometer," City University of Hong Kong, Department of Physics and Material Science, Bachelor of Science (Hons) in Applied Physics 2010-2011, Project Report submitted Mar. 2011, 40 pages.

* cited by examiner

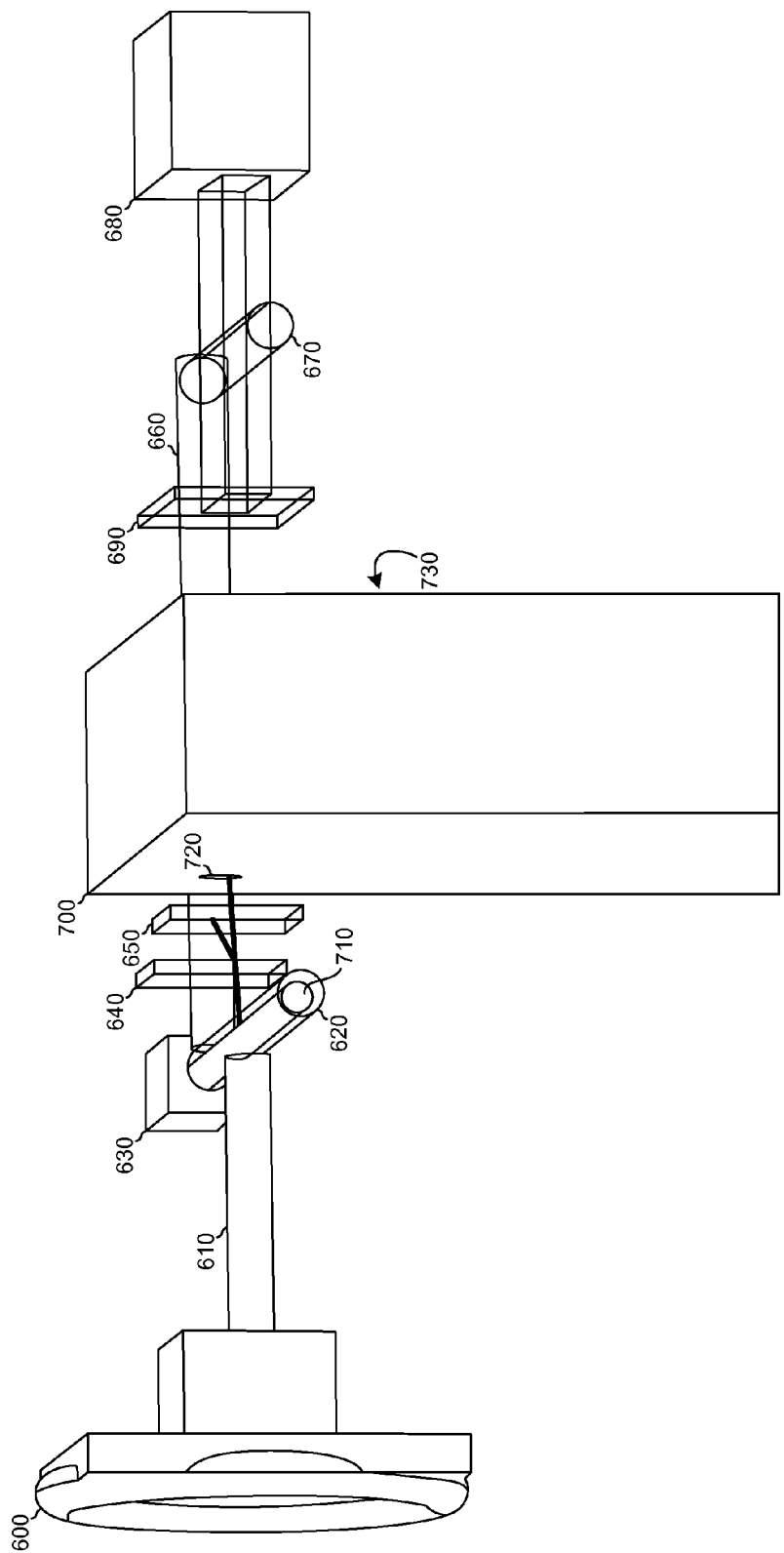

MOBILE MICRO-LAB FOR CHEMICAL ANALYSIS OF FLUIDS

CROSS REFERENCE TO RELATED APPLICATIONS

This disclosure claims benefit from U.S. Provisional Application 62/011,971, entitled MOBILE MICRO-LAB FOR CHEMICAL ANALYSIS OF FLUIDS, filed Jun. 13, 2014, the contents of which are incorporated by reference herein.

BACKGROUND

This disclosure relates to molecular analysis of fluids, and particles and gases suspended in fluids. Embodiments of the invention include a mobile micro-lab that performs on-site chemical analysis for both laymen and professionals. Among the many applications of such general purpose chemical analysis, it is particularly suited for the analysis of organic chemicals. Therefore, applications include, but are not limited to, chemical analysis in biology, pharmaceuticals, medical diagnostic tests of body fluids, nutrition, pathogen and toxin detection. The capability of this micro-lab compares favorably with that of the combined capability of several sets of massive systems traditionally used within laboratories. Such massive analysis systems include, but are not limited to multiple electrophoresis systems including dye, stain and analysis post processing, isoelectric focusing and Raman and infra-red spectrometers.

Medical applications include preventative medicine, sports medicine, supplementary to check-ups, screening for pathologies, monitoring for feedback of treatments including medications, diet, exercise, sleep, misc. lifestyle changes, and general chemical analysis of body fluids. It provides individuals and remote health care providers with rapid, frequent and inexpensive access to vital health status information previously requiring long waits, fees and invasive procedures or denied by insurance. It enables remote- and self-testing and screening for many things formerly requiring blood and other body fluids to be sent to in a laboratory. Its software optionally uses supplementary contextual information such as time of day (subject's circadian cycle phase), medical history, intake including dietary, fluids, medications, stress levels, sleep, etc. to determine appropriate threshold limits for results. For example, fluctuation in glucose levels have afore been too high in interstitial tissue to use without calibration. However, by using contextual information such as dietary intake, activity monitoring, time of day (circadian cycle, body temperature, etc.) to determine statistical biases, relative glucose levels may be determined.

Its hardware platform serves a growing abundance of functions through software applications that run fluid biochemical analysis tests and analyze the resulting raw measurement data. The design is modular and scalable, allowing for very small footprints.

It can optionally extract interstitial fluid, the fluid lining the cells, to determine chemicals entering and leaving the cells. The interstitial fluid (IF) is extracted without discomfort using minimally invasive micro-needles. Other fluids such as blood, urine and saliva may be analyzed and compared with normative references, taking into account individual norms, history and circadian cycles. Results can show normal or abnormal constituent concentrations, in some cases for direct diagnosis and in others indicating further testing may be warranted and/or a physician or other health care professional should be consulted.

Information is gathered from the fluid specimen using a unique combination of molecular spectroscopy, multiple-pass dual electrophoresis, electrohydrodynamics, video capture, video processing including spatial spectral tracking, and adaptive measurement and analysis algorithms. With the default configuration, intermediate measurement results include multiple moving object Raman spectra (including from optional surface enhanced Raman spectroscopy or SERS) of free flow electrophoresis, multiple moving object infra-red spectra of gel electrophoresis (including optional gradient gel electrophoresis for determining pH of component). The electrophoretic voltage, current or power can be controlled as DC, pulsed, sinusoidal or arbitrary wave. The electric fields are applied across a selection of pairs of multiple electrodes located throughout the interconnected tube system. In the case of sinusoidal wave electric fields, the phase lag in velocity (for each particular frequency used) of each component may be used to further determine unique mobility characteristics. Advanced video processing algorithms, with patents pending, provide greatly enhanced spectral line resolution and accuracy, component tracking (including with neutral, positive and negative buoyancy or sediment), velocity measurement, band smearing, which enable the calculation of molecular charge, molecular weight, pH, dielectric and conductivity. Principal component analysis applied to individual spectra enables analysis of chemicals not sufficiently resolved by electrophoresis. An optional recycling tube can enables augmented separation nearly equivalent to arbitrarily long electrophoresis lanes.

SUMMARY OF EMBODIMENTS

Embodiments of the invention include a method of performing chemical analysis of fluids using a mobile device. For a solution being analyzed, such methods include spatially separating charged particles within the solution, separating electromagnetic radiation of the solution, capturing as a series, successive, two-dimensional images of a plurality of dynamically, spatially separated electromagnetic spectra, and detecting substances within the solution based on a combination of relative spatial and electromagnetic spectral images. In some embodiments, spatially separating charged particles within the solution includes performing a free flow electrophoresis on the solution and performing gel electrophoresis on the solution. The gel electrophoresis may be isoelectric focused (IEF) electrophoresis utilizing a gel matrix with a pH gradient.

Spatially separating charged particles within the solution can include applying electric fields across a selection of pairs of multiple electrodes located within an interconnected tube system and modulating the electric fields, such as by applying a sinusoidal wave. Detecting substances within the solution may include, for each frequency of the sinusoidal wave, analyzing a phase lag in a velocity of the sinusoidal wave propagating through the solution.

In some embodiments, separating electromagnetic radiation of the solution may include performing Raman spectroscopy and/or performing infrared spectroscopy.

Capturing successive, two-dimensional images may include capturing images with two cameras on opposite sides of the mobile device. Performing infrared spectroscopy may include capturing an infrared image using a CCD camera without a near infrared (NIR) filter or capturing an infrared image with an infrared camera.

In some embodiments, spatially separating charged particles within the solution may include spatial tracking of moving spectra across successive images to form spatial tracking trajectories and calculating or measuring respective substance properties based on one or more selected from the group of: the spatial tracking trajectories, dynamic control voltages and drive current, molecular charge, molecular weight, pH, dielectric and conductivity. It may further include storing the calculated or measured respective substance properties as data and analyzing the stored substance properties data.

Determining charge to molecular weight ratio of charged particles in solution may include measuring increases in 2-D Raman spectrum line width due to blurring by the average excursion of sinusoidal molecular motion as a function of molecular weight and charge, as well as control voltage amplitude and frequency.

In some embodiments, fluid may be introduced to an entry port of the mobile device through a vacuum based suction cup having micro-needles.

In some embodiments, separating electromagnetic radiation of the solution may include transmitting electromagnetic radiation through the solution, or gathering electromagnetic radiation reflected from the solution or emitted from the solution.

In some embodiments, analyzing substances within the solution may be based on a combination of relative spatial and electromagnetic spectral images.

Methods may also include quantifying substances within the solution based on a combination of relative spatial and electromagnetic spectral images.

In some embodiments, detecting substances within the solution based on a combination of relative spatial and electromagnetic spectral images may include detecting substances within the solution based on a combination of temporal or temporal derivatives of relative spatial and electromagnetic spectral images. Also, analyzing the stored substance properties data may include, for substances not sufficiently resolved by spatial separation and spectral signature directly, principal component analysis or non-negative least squared error.

Some embodiments of the invention may include method of transporting substances in a fluid through a device by generating a fluid pressure gradient in the fluid using one or more pumps in the device, controllably steering the flow of solution by operating one or more values that allow fluid to pass when the one or more valves are not closed and that prevent the fluid from passing when the one or more valves are closed, and moving charged particles in solution by means of electrophoresis. Moving charged particles in solution by means of electrophoresis may include using a recycling tube to enable augmented separation.

Some embodiments of the invention may include a method of analyzing substances within a fluid by using a first imaging device to capture a first plurality of chemical analysis images, and using a second imaging device to capture a second plurality of chemical analysis images. The first imaging device and the second imaging device may be on opposite sides of a mobile device.

In some embodiments capturing the first plurality of chemical analysis images may include separating the electromagnetic radiation by means of a Raman spectrometry to form a spectogram image, and capturing the second plurality of chemical analysis images may include separating the electromagnetic radiation by means of infrared spectrometry to form a spectogram image. In some embodiments, the respective spectrograms are two-dimensional, where a first dimension represents spatial separation of substances and the second represents electromagnetic radiation separation. Spatial separation may include separating the electromagnetic radiation by means of a free flow electrophoresis and separating the electromagnetic radiation by means of a gel electrophoresis.

BRIEF DESCRIPTION OF THE FIGURES

FIG. 3 is a mechanical diagram the mobile micro-lab system showing the relative positions of the principal components including two electrophoresis tubes, two spectrometers and respective electromagnetic radiation sources. Also shown is an optional suction cup with micro-needles for collecting interstial fluid.

DESCRIPTION

Figure 1:
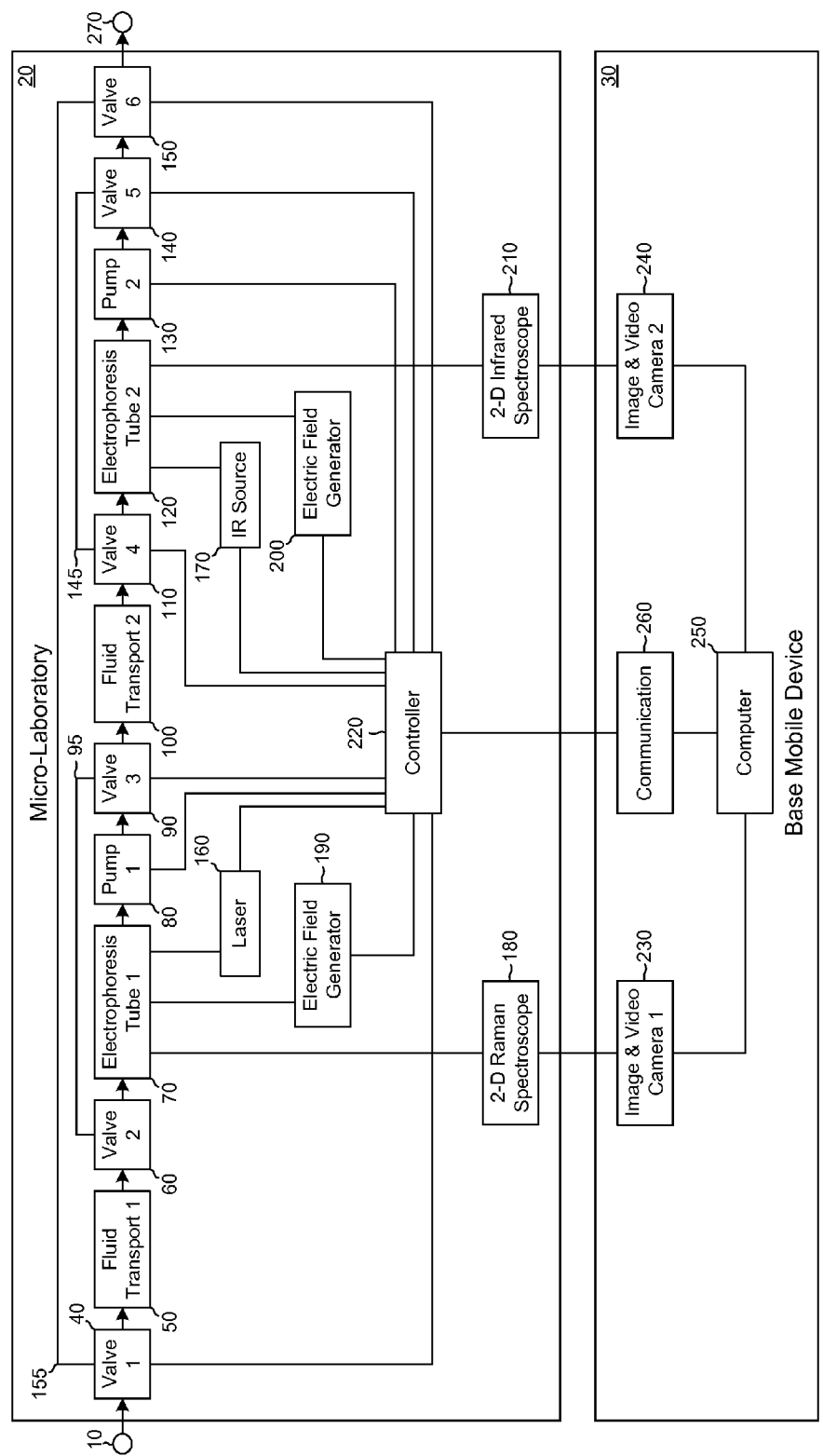
FIG. 1 is a block diagram the mobile micro-lab system according to embodiments of the invention.

As shown in FIG. 1, the fluid 10 enters the micro-lab 20, that is in turn controlled and monitored by a computer based device such as a mobile device 30. The system is controlled by a computer or equivalent digital device (controller or FPGA) 250 through a communication link 260 with the micro-lab 20.

The fluid enters through a first valve 40 and moves into a first transparent tube 50 via a pressure difference created by a first pump 80 and/or a second pump 130. In one embodiment pumps are micro-pumps. The fluid flow direction throughout the network of tubes is controlled by a set of valves 40, 60, 90, 110, 130, 140 and 150. Electrodes throughout the structure of tubes 50, 70, 95, 100, 120, 145, valves 40, 60, 90, 110, 130, 140, 150 and pumps 80, 130 are used to apply electrophoretic forces to move, separate and concentrate charged particles. Neutral particles are moved via convection using the pumps. In an embodiment, electrodes are rings at the interface of components, for example, where a tube connects to another tube. In another embodiment, ring electrodes are additionally placed near the middle of tubes, but out of the view of cameras 230 and 240.

In one embodiment, the first transparent tube 50 is a free solution electrophoresis chamber, where voltage signals are applied to electrodes at either end, causing charged particles to move towards their respective opposites. In one embodiment, the voltage waveforms vary according to the particular chemical analysis being performed. For example, the electrodes are pulsed, and when off in one embodiment, a laser 160 is enabled as the light source for a two-dimensional (2-D) Raman spectroscope 180 (nominally composed of a frequency separator, such as a diffraction grating, and an optical rejection filter) where the specimen is spread across the length of the first electrophoresis tube 70, and the first camera 230 captures the resulting two-dimensional spectrogram. From the laser 70, a laser beam is sent down the length of the first electrophoresis tube 70. In one embodiment, the mechanical orientation of respective components is as shown in FIG. 3: Laser 630 creates a laser beam which traverses a tube 620 which is optically transparent over the wavelengths of interest, with orthogonally oriented Raman scattered light reaching camera lens 720 after being separated by wavelength (frequency) separator, in some embodiments a diffraction grating, 640, and a filter to block the laser's direct light 650 are included, while allowing some direct light along the edge of the captured image. The Raman spectrometer creates a 2-D spectrum with the wavelengths spread orthogonal to the length of the electrophoresis tube 620, which is approximately in the vertical in FIG. 3. The quantum vibrations and rotations from the specimen molecule components are each unique to the respective portion of each unique molecule. The unique spectra move along the length of the tube in the velocity (direction and speed) according to charge, voltage, molecular weight, and other factors. The voltage may be modulated. In some embodiments the generated controlled voltage, current or power may have the form of sinusoidal waves of various amplitudes and frequencies and/or pulsed on and off with various duty cycles, or controlled from an arbitrary waveform generator in order to determine information from the relative motion of the constituent molecules.

In some embodiments the lens 720 may itself be a microscope lens or may be used in conjunction with one or more additional lenses, including but not limited to a lens placed between electrophoresis tube 620 and diffraction grating 640, or between the diffraction grating 640 and optical filter 650, or between optical filter 650 and nominal camera lens 720, to produce microscope grade magnification, including with zoom capability, resulting in a 2-D spectrum which can track object motion in resolution on the order of microns. In addition, in some such embodiments with microscopic imaging, the voltage modulation frequencies may be sufficiently high such that the time constant for charged molecules reaching terminal velocities in solution (due to fluid viscosity, etc.) may be used as a low pass filter in the transfer function of voltage to charged molecule motion. With sufficiently large molecules and charge, sufficient voltage and frequency, and sufficient magnification and resolution (including image enhancement), the corresponding 2-D Raman spectrum is blurred by the average excursion of sinusoidal molecular motion.

Each of these 2-D Raman spectra are captured with a camera with at least 2 filters, in some embodiments red and green filters (such as found in conventional RGB cameras as in typical commercially available electronic cameras in smart phones and other mobile devices). The frequency discrimination given by the filters is used to further resolve and accurately identify the wavelengths of spectral peaks in the 2-D Raman spectra. Further image reconstruction and spectral enhancement is performed as per Kevin Ferguson, "OPTICAL SPECTROMETER WITH ENHANCED SPECTRAL RESOLUTION FROM AN UNREGISTERED TRISTIMULUS DETECTOR", U.S. patent application Ser. No. 14/302,291, filed Jun. 11, 2014, which is incorporated by reference herein. Thus, for each unique spatial location where spectra are found, respective unique Raman spectra are also found. And each of these objects may be tracked over time to determine respective speeds and polarities given the electronic pulses. After the objects have cleared the Raman spectrometer area, the polarity of pulses is reversed to capture images of the 2-D Raman spectra of the oppositely charged particles in a similar manner.

Figure 2:
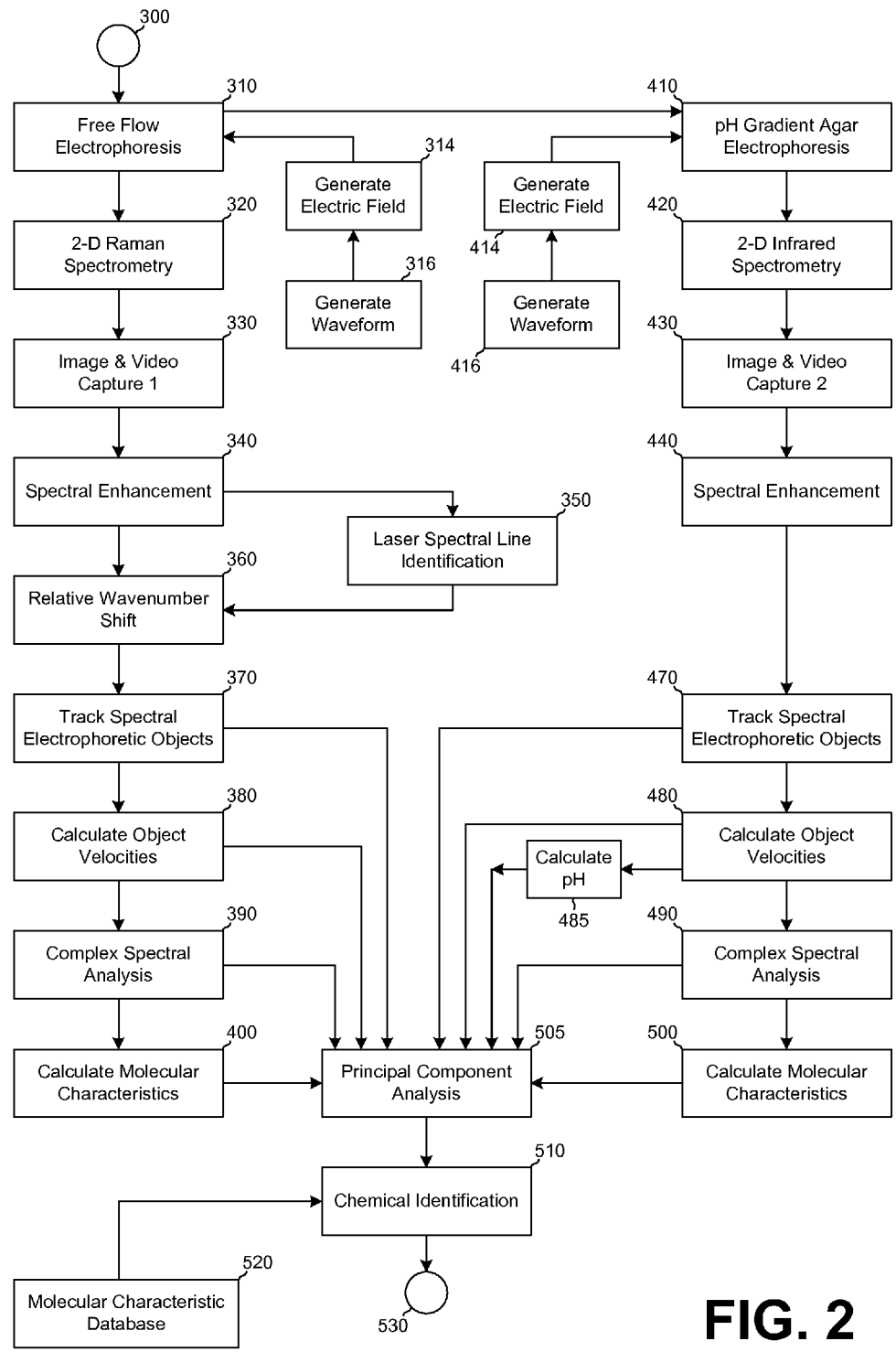
FIG. 2 is a flow diagram of mobile micro-lab processing methods according to embodiments of the invention.

As shown method diagram of FIG. 2, the specimen 300 is subjected to free flow electrophoresis 310 that separates charged particles (including separate molecules) among which are polarizable molecules and functional groups subject to Raman scattering that is detected by the use of a 2-D Raman spectrometer 320 that produces a 2-D spectrum image which is captured by a imaging device 330 and improved and spectrally enhanced by the before mentioned '291 patent application, in an operation 340.

The edge of the spectrogram image includes appropriately attenuated laser light in order to detect the laser wavelength precisely (Laser Spectral Line Identification 350) for the purpose of calculating Raman shift 360. Thus, for corresponding to each position traversing electrophoresis tube (70 of FIG. 1, 620 of FIG. 3), the corresponding Raman shift spectra is determined. Unique spectra correspond to unique chemical components which are tracked by object tracking 370. Charged particles in motion due to electrophoresis are tracked and therefore the velocities of each are calculated 380. In some embodiments such as with high frequency electrophoresis voltage modulation (from waveform generation due to 316 and electric field generation 314) and microscope imaging, complex spectral analysis may be applied or other analysis may be applied to the data so far gathered as represented in 390.

The electric field generated by a power supply 314 may use voltage, current or power control. Regardless of which is used for control, each of voltage, current and power is measured across each electrode. By comparing time trajectories of voltage and current, complex impedance of the fluid load may be tracked over time for each volume between respective pairs of electrodes.

Further context may be used to further determine molecular characteristics 400. In one embodiment, the terminal velocity of a spectrum object is used to determine the corresponding charge of the corresponding particle.

Referring again to FIG. 1, once polarizable molecules have been measured using the 2-D Raman spectrometer, and charge characteristics determined with free flow electrophoresis, the specimen fluid is moved through a first pump 80 which is nominally as an open valve to minimize turbulence and through a third valve 90. At this point, the fluid may either be moved on to a second fluid transport tube 100, or circulated back to the second valve 60 for further electrophoretic separation. This transport may be by convection to fluid transport tube 100 using a second pump 130, or alternatively, for further electrophoresis, only charged particles are moved using appropriate alternate voltage states of electrodes to move the particles through this stated path return tube 95 through the second valve 60 and back into the first electrophoresis tube 70. The fluid specimen that has left the first electrophoresis cycle area of 60, 70, 80, 90 and 95, continues through to a second transparent tube 100, a forth valve 110 and into a second electrophoresis tube 120.

In some embodiments, the second electrophoresis tube 120 contains a gel matrix with a pH gradient for isoelectric focused (IEF) electrophoresis. The charged particles again are moved by applying voltage (controlled by voltage, current or power) across electrodes at either end of the transparent tube. However, in this second chamber 120, the gel matrix with increasing pH across the length of the tube causes each charged molecule to stop once it has reached its respective isoelectric point. Using infra-red source 170, and an infrared spectroscope 210 creates a respective spectrogram for each unique absorption spectra across the length of the tube 120 and this unique 2-D spectrum is captured by camera 240. The camera 240 may be a commercially available camera with one or more of the red, green and blue optical filters and IR blocking filter replaced with those most appropriate for frequency discrimination in the infra-red band of interest. In one embodiment, a specialized capture mechanism is used that is optimal for far infra-red. Note that the infrared spectrum is generally complementary to the Raman spectrum in that they tend to be most sensitive to different molecular phenomena.

In an alternative embodiment, the second electrophoresis tube 120 has a gel without any pH gradient. Thus there is no isoelectric point to cause 0 charge for an otherwise charged particle. Instead the tube 120 is used for traditional gel electrophoresis. In some such embodiments, multiple passes through the gel may be used to further separate charged particles. This may be performed by opening pump 130, valve 140 and valve 110 appropriately for allowing recirculation back to the connection between valve 110 and electrophoresis tube 120. Again, as in the case of the first electrophoresis tube 70 having recirculation by way of tube 95, by appropriately applying voltages at electrodes along this path, charged particles may be recirculated and further separated.

Referring again to FIG. 3 showing mechanical orientation, fluid enters the second electrophoresis tube 670 from tube 660. This second tube 670 is transparent to infrared. The infrared frequency separator (a diffraction grating in some embodiments) 690 separates the wavelengths (frequencies) for each portion along the tube 670. The infrared camera 730 captures the resulting 2-dimensional infra-red spectrogram image.

In an embodiment, both cameras 720 and 730 belong to a mobile device such as a smart phone. In such an embodiment, the phone may be attached to the micro-lab.

Referring again to FIG. 2, the results of isoelectric focused electrophoresis from 410 are converted in to a 2-D spectrum using 2-D infra-red spectrometry 420, captured by image and video capture 430, with spectral enhancements using techniques described in the above-referenced '291 patent application. Thus, the molecules again can be tracked (470) to determine velocities (480) for each unique spectrum, and in addition, the pH (485) and total charge based on isoelectric point determined by where each molecule stops in the gel. From the velocity and the charge, the size of each molecule may be determined.

Analysis of the relationship between voltage, current and motion (as described earlier relating to 390) is applied via complex spectral analysis 490, and as with 400, molecular characteristics are calculated 500: Once no more motion is detected in the gel, analysis of the data may be completed. The data collected for each molecule at this point includes: Complementary Raman and IR spectra, charge, conductivity estimates, and in some cases size (molecular weight).

The spectra area analyzed using principal component analysis (505) along with the context of the associated measured parameters and image trajectories to determine most likely spectra and quantity of each individual molecular component in the specimen. From this, most major and many minor constituent molecules may be identified (510) by comparing the most likely individual component spectra and other measured parameters with the corresponding spectra and parameters in the chemical database 520.

The output of method is 530, a list of chemicals identified, quantified and the corresponding measured parameters.

Although specific embodiments of the invention have been illustrated and described for purposes if illustration, it will be understood that various modifications may be made without departing from the spirit and scope of the invention. Accordingly, the invention should not be limited except as by the appended claims.

What is claimed is:

1. A method of performing chemical analysis of fluids using a mobile device, comprising, for a solution being analyzed:
   spatially separating charged particles within the solution;
   separating electromagnetic radiation of the solution;
   analyzing separated particles within the solution by:
      spatial tracking of moving spectra across successive images to form spatial tracking trajectories,
      calculating or measuring respective substance properties based on one or more selected from the group of: the spatial tracking trajectories, dynamic control voltages, dynamic drive current, molecular charge, molecular weight, pH, dielectric and conductivity,
      storing the calculated or measured respective substance properties as data, and
      analyzing the stored substance properties data;
   for at least some of a plurality of substances within the solution, capturing as a series, successive, two-dimensional images of a plurality of dynamically, spatially separated electromagnetic spectra; and
   detecting substances within the solution based on a combination of relative spatial and electromagnetic spectral images.

2. The method as recited in claim 1 wherein spatially separating charged particles within the solution comprises:
   performing a free flow electrophoresis on the solution; and
   performing gel electrophoresis on the solution.

3. The method as recited in claim 2 wherein performing gel electrophoresis comprises performing isoelectric focused (IEF) electrophoresis utilizing a gel matrix with a pH gradient.

4. The method as recited in claim 1 wherein the spatially separating charged particles within the solution includes:
   applying electric fields across a selection of pairs of multiple electrodes located within an interconnected tube system; and
   modulating the electric fields.

5. The method as recited in claim 4 wherein modulating the electric field comprises applying a sinusoidal wave and wherein detecting substances within the solution comprises, for each frequency of the sinusoidal wave, analyzing a phase lag in a velocity of the sinusoidal wave propagating through the solution.

6. The method as recited in claim 1 wherein separating electromagnetic radiation of the solution comprises:
   performing Raman spectroscopy; and
   performing infrared spectroscopy.

7. The method as recited in claim 1 wherein capturing successive, two-dimensional images comprises capturing images with two cameras on opposite sides of the mobile device.

8. The method as recited in claim 6 wherein performing infrared spectroscopy comprises capturing an infrared image using a CCD camera without a near infrared (NIR) filter.

9. The method as recited in claim 6 wherein performing infrared spectroscopy comprises capturing an infrared image with an infrared camera.

10. The method as recited in claim 1 wherein the means for determining charge to molecular weight ratio of charged particles in solution comprises:
    measuring increases in 2-D Raman spectrum line width due to blurring by the average excursion of sinusoidal molecular motion as a function of molecular weight and charge, as well as control voltage amplitude and frequency.

11. The method as recited in claim 1, further comprising:
    introducing a fluid into an entry port of the mobile device through a vacuum based suction cup having microneedles.

12. The method as recited in claim 1, in which separating electromagnetic radiation of the solution comprises transmitting electromagnetic radiation through the solution, or gathering electromagnetic radiation reflected from the solution or emitted from the solution.

13. The method as recited in claim 1, further comprising:
identifying substances within the solution based on a combination of relative spatial and electromagnetic spectral images.

14. The method as recited in claim 1, further comprising:
quantifying substances within the solution based on a combination of relative spatial and electromagnetic spectral images.

15. The method as recited in claim 1, in which:
detecting substances within the solution based on a combination of relative spatial and electromagnetic spectral images comprises detecting substances within the solution based on a combination of temporal or temporal derivatives of relative spatial and electromagnetic spectral images.

16. The method as recited in claim 1, in which:
analyzing the stored substance properties data comprises, for substances not sufficiently resolved by spatial separation and spectral signature directly, principal component analysis or non-negative least squared error.

17. A method of performing chemical analysis of fluids using a mobile device, comprising, for a solution being analyzed:
spatially separating charged particles within the solution;
spatially tracking moving spectra across successive images to form spatial tracking trajectories;
calculating or measuring respective substance properties based on the spatial tracking trajectories;
analyzing the calculated or measured respective substance properties;
for at least some of a plurality of substances within the solution, capturing as a series, successive, two-dimensional images of a plurality of dynamically, spatially separated electromagnetic spectra; and
detecting substances within the solution based on a combination of spatial and electromagnetic spectral images.

18. The method of claim 17, further comprising:
calculating or measuring respective substance properties based on dynamic control voltages.

19. The method of claim 17, further comprising:
calculating or measuring respective substance properties based on dynamic drive current.

20. The method of claim 17, further comprising:
calculating or measuring respective substance properties based on molecular charge.

21. The method of claim 17, further comprising:
calculating or measuring respective substance properties based on molecular weight.

22. The method of claim 17, further comprising:
calculating or measuring respective substance properties based on molecular pH.

23. The method of claim 17, further comprising:
calculating or measuring respective substance properties based on molecular charge.

24. The method of claim 17, further comprising:
calculating or measuring respective substance properties based on dielectric properties.

25. The method of claim 17, further comprising:
calculating or measuring respective substance properties based on electrical conductivity.

26. The method of claim 17, further comprising storing the calculated or measured respective substance properties as data, and in which analyzing the calculated or measured respective substance properties comprises analyzing the stored substance properties data.

* * * * *